United States Patent [19]

St. George et al.

[11] Patent Number: 5,731,468
[45] Date of Patent: Mar. 24, 1998

[54] PREPARATION OF DISODIUM ETHYLENEDIAMINE-N,N'-DISUCCINATE

[75] Inventors: George M. St. George, Lake Jackson; David A. Wilson, Richwood, both of Tex.

[73] Assignee: The Dow Chemical Company, Midland, Mich.

[21] Appl. No.: 832,555

[22] Filed: Apr. 3, 1997

[51] Int. Cl.$^6$ .................................................. C07C 229/00
[52] U.S. Cl. ........................................... 562/565; 562/554
[58] Field of Search ................................... 562/554, 565

[56] References Cited

U.S. PATENT DOCUMENTS 3,158,635  11/1964  Kezerian et al. ................... 260/429
5,466,867  11/1995  Lin et al. ............................ 562/554
5,554,791  9/1996   Lin et al. ............................ 562/565
5,569,443  10/1996  Wilson ............................... 423/576.6
5,587,512  12/1996  Lin et al. ............................ 562/565

FOREIGN PATENT DOCUMENTS 0 687950  5/1995  European Pat. Off. .
95/12570  5/1995  WIPO .

*Primary Examiner*—Michael L. Shippen

[57]  ABSTRACT

A process is disclosed for isolating the disodium salt of racemic and meso isomers of ethylenediamine-N,N'-disuccinic acid from alkaline aqueous solutions.

14 Claims, No Drawings

PREPARATION OF DISODIUM ETHYLENEDIAMINE-N,N'-DISUCCINATE

BACKGROUND OF THE INVENTION

Chelants, or chelating agents, are compounds which form coordinate covalent bonds with a metal ion to form chelates. Chelates are coordination compounds in which a central metal atom is bonded to two or more other atoms in at least one other molecule (the chelant) such that at least one heterocyclic ring is formed with the metal atom as part of the ring.

Chelants are used in a variety of applications including food processing, soaps, detergents, cleaning products, personal care products, pharmaceuticals, pulp and paper processing, water treatment, metalworking and metal plating solutions, textile processing solutions, fertilizers, animal feeds, herbicides, rubber and polymer chemistry, photofinishing, and oil field chemistry. Some of these activities result in chelants entering the environment. For instance, agricultural uses or detergent uses may result in measurable quantities of the chelants being present in water. It is, therefore, desirable that chelants degrade after use. Of particular interest are chelating agents which are biodegradable, that is, susceptible to degradation by microorganisms.

Ethylenediamine-N,N'-disuccinic acid (EDDS) has been found to be useful in several applications where ethylenediamine-N,N,N',N'-tetraacetic acid (EDTA) has been used. For example, EP patent application 0 532 003, published Mar. 17, 1993, describes the use of EDDS in photographic processing; World patent application 9428464, published Dec. 8, 1994, describes the use of EDDS in electroless plating; U.S. Pat. No. 5,569,443, published Oct. 29, 1996, describes the use of EDDS in hydrogen sulfide abatement; and U.S. Pat. No. 4,704,233 issued Nov. 3, 1987 describes the use of EDDS in detergent formulations. The enhanced biodegradability of EDDS relative to EDTA makes EDDS a favorable replacement for EDTA where a faster rate of biodegradation is desired.

A challenge in the production of EDDS is its preparation in an economical, pure form. EDDS is generally obtained from reaction mixtures containing salts of EDDS by acidification of the mixture to a pH of about 2. For example, Neal and Rose (Inorg. Chem., 7, 2405 (1968)) describe the reaction of L-aspartic acid with ethylene dibromide in the presence of base to give a mixture containing the tetrasodium salt of S,S-EDDS which, upon acidification, gives crude S,S-EDDS. Neutralizing the crude acid with base and re-acidifying gives pure S,S-EDDS. Similarly, the procedure of Kezerian and Ramsey (U.S. Pat. No. 3,158,635, published Nov. 24, 1964) combines sodium maleate with ethylenediamine to give a mixture of products containing racemic and meso tetrasodium EDDS. In order to isolate pure EDDS acid, the reaction mixture was acidified to pH about 2, precipitating racemic/meso EDDS acid. The preparation of the disodium EDDS salt (tetrahydrate and anhydrous) from EDDS acid was accomplished by the addition of two equivalents of NaOH followed by crystallization. Preparation of disodium EDDS by the procedure of Kezerian et. al. requires the addition of four equivalents of acid and six equivalents of base. Recent disclosures by Patel, et al. (World patent application 9512570, published May 11, 1995) and Lin, et al. (U.S. Pat. No. 5,466,867, published Nov. 14, 1995) also describe methods for obtaining purified EDDS acid. These methods require complete neutralization of the tetrasodium salt (with four equivalents of acid), resulting in four equivalents of salt as a by-product.

It would be desirable to have an economical method for isolating a pure form of EDDS from a reaction mixture in good yield utilizing a minimum of raw materials and with less salt by-product.

SUMMARY OF THE INVENTION

A pure form of racemic/meso EDDS, specifically the disodium salt tetrahydrate, can be obtained from crude reaction solution mixtures containing the sodium salts by acidification of the solution to a pH of about 5 to about 10.

In one embodiment, the invention is a method for preparing a disodium salt of ethylenediamine-N,N'-disuccinic acid from an alkaline aqueous solution containing a racemic and meso mixture of sodium salts of ethylenediamine-N,N'-disuccinate isomers comprising adjusting the pH of the alkaline solution to between about 5 to about 10 by the addition of an acid and recovery of the solid disodium salt.

In another aspect, the present invention is a method for the preparation of a disodium salt of EDDS comprising (a) reacting maleate with ethylenediamine in an alkaline aqueous solution to form sodium salts of EDDS and (b) precipitating disodium EDDS from the aqueous solution of sodium salts of EDDS by adjusting the pH to between about 5 to about 10 with an acid.

The methods of the present invention allow the isolation of a purified form of EDDS from reaction mixtures without the necessity of forming the free acid. The method for obtaining the disodium salt is particularly advantageous in applications where the free acid is not required, such as where the chelating agent will be combined with a metal ion, for example, for use in photography where an iron chelate is used. In addition, a greater amount of disodium EDDS is recovered by the methods of the present invention.

DETAILED DESCRIPTION OF THE INVENTION

It has been found that a form of EDDS, specifically the disodium salt tetrahydrate of the racemic/meso isomer mixture, can be obtained in high yield and purity from a solution mixture. Generally the isomer mixture is that obtained from non-stereospecific processes known in the art for the preparation of EDDS, for example, EDDS formed by the reaction of DL-aspartic acid with ethylene dibromide. Preferably the isomer mixture is that obtained when maleate, ethylenediamine and caustic (NaOH) are reacted under conditions to produce tetra-sodium EDDS as disclosed in U.S. Pat. No. 3,158,635, the disclosure of which is incorporated herein by reference.

The isomer mixtures used in the present invention are generally prepared under alkaline conditions. It has been unexpectedly found that the disodium salt of EDDS can be separated from unreacted starting materials and by-products by acidifying the solution to a pH between about 5 to about 10. Preferably the pH is adjusted to between about 6 to about 8. In this pH range, by-products such as maleate; fumarate; and ethylenediamine-N-monosuccinate (EDMS) are soluble and are easily removed from the mostly insoluble EDDS salt. This method requires half the amount of acid versus that which is required to precipitate the free acid of EDDS. This results in an economical and practical process for separating EDDS from the reaction mixture as a purified disodium salt.

Reaction conditions are generally selected so that the amount of EDDS present, before the pH adjustment, is from about 10 to about 60 weight percent of the solution. Preferably the EDDS is present at a concentration of about 15 to about 50 percent by weight of the solution. More preferably the amount of EDDS present is from about 20 to about 50 percent by weight of the solution.

The isolation of racemic/meso disodium EDDS by this method is unexpected, as neither the dipotassium salt nor the diammonium salt of EDDS can be isolated by this method. Also surprisingly, the disodium salt of S,S-EDDS cannot be isolated by this method. It was found that the S,S-isomer co-precipitates with the other isomers in the racemic/meso mix but does not precipitate when it is the only isomer in solution. Furthermore, in the absence of the meso-isomer, a mixture of disodium [S,S]-and [R,R]-EDDS precipitates in low yield.

The pH adjustment may be effected by a number of inorganic and organic acids, including, but not limited to, hydrochloric, hydrobromic, sulfuric, nitric, phosphoric, perchloric, formic, acetic, chloroacetic, dichloroacetic, trichloroacetic, trifluoroacetic, propionic, butyric, methylsulfonic, trifluoromethylsulfonic, ethylsulfonic, methylphosphonic, and ethylphosphonic acids. Preferably the acid is a strong mineral acid. More preferred are acids which are inexpensive, water-soluble, strong acids having water-soluble sodium salts. The preferred acids include hydrochloric, sulfuric, nitric, phosphoric, acetic and mixtures thereof. The most preferred acids are sulfuric, hydrochloric and nitric.

The addition of the acid to the reaction mixture containing sodium salts of EDDS can be done using conventional equipment. The pH adjustment may be performed in the temperature range 0°–110° C. and preferably 5°–90° C. More preferably the acid addition is done in the temperature range of about 10° to about 80° C.

The insoluble disodium EDDS obtained by the process of the present invention can be recovered by standard procedures for the separation of liquid-solid systems. Such processes include filtration and centrifugation. Generally for ease of operation, the disodium EDDS is recovered by filtration. If desired, the product recovered can be further purified by washing the obtained crude material (for example the solid obtained upon filtration) with water.

The invention will be further clarified by a consideration of the following examples, which are intended to be purely exemplary of the present invention. All percents are by weight unless otherwise indicated.

EXAMPLE 1

A 100-mL beaker was charged with 35 g of an aqueous process solution containing 39.3 percent $Na_4EDDS$ (13.8 g, 0.0362 mole); 5.17 percent $Na_2EDMS$ (1.81 g, 0.0082 mole); 1.00 percent disodium fumarate (0.35 g, 0.0022 mole); and 2.07 percent disodium maleate (0.72 g, 0.0045 mole). The tetra-sodium EDDS mixture was obtained by the reaction of sodium maleate with ethylenediamine as disclosed in U.S. Pat. No. 3,158,635. Concentrated nitric acid was added until the pH was 7.0. The mixture was stirred using a magnetic stir bar for about four hours at ambient temperature. The mixture was allowed to stand overnight to complete the precipitation. Filtration of the mixture gave a white solid that was vacuum-dried (80° C). The yield was 12.5 g of $Na_2EDDS\cdot4H_2O$ (0.0306 mole, 84.6 percent yield) essentially free of EDMS, maleate, and fumarate as determined by NMR. That the product is a tetrahydrate was verified by elemental analysis: Calc. for $Na_2EDDS\cdot4H_2O$: C 29.42, H 5.43, N 6.86, Na 11.26 percent. Found: C 27.64, H 5.72, N 6.67, Na 11.76 percent.

EXAMPLES 2, 3, AND 4

These examples were run in the same manner as Example 1, except that the pH was adjusted to 5, 6, and 8, respectively. The recovered crude yields were 16.2 g, 15.8 g, and 9.5 g respectively. The sample which precipitated at pH 5 also contained maleate and fumarate.

COMPARATIVE EXAMPLE A (Preparation of EDDS acid)

A beaker was charged with maleic acid (120.5 g, 1.03 mole); deionized water (120 g); and 50 percent aqueous NaOH (167 g, 2.08 mole). The mixture was stirred until dissolution occurred; the resulting solution was transferred to a 1-liter, stainless-steel autoclave, using 40 g deionized water as a rinse. Ethylenediamine (31.0 g, 0.51 mole) was added over a ten-minute period; and the autoclave was sealed. The mixture was stirred and heated at 140° C. for nine hours and then allowed to cool to ambient temperature. The product solution was acidified to a pH of about 2 with 37 percent aqueous HCl, resulting in the precipitation of racemic/meso EDDS acid. When the precipitation was complete, the product was removed by filtration; washed with deionized water (2×300 mL); and dried overnight under vacuum at 60° C. The yield of EDDS acid, shown to be pure by $^1H$- and $^{13}C$-nmr, was 108 g (0.37 mole, 72 percent).

COMPARATIVE EXAMPLE B

A 200-mL beaker was charged with EDDS acid made in the manner of Comparative Example A (29.2 g, 0.100 mole) and water (71 g). Fifty percent aqueous NaOH was added until the pH reached 7.0 (17.6 g, 0.220 mole). Precipitation was complete in one day. Filtration and vacuum-drying gave 18.2 g of $Na_2EDDS\cdot4H_2O$ (0.045 mole, 45 percent recovery).

Comparative examples A and B show the yield of product obtained by these procedures is substantially less than that obtained by the method of the present invention.

COMPARATIVE EXAMPLES C and D

These examples were performed in the manner of Comparative Example B, except that in place of the aqueous NaOH, 45 percent aqueous KOH (25 g, 0.200 mole) and 28 percent aqueous $NH_3$ (14.8 g, 0.240 mole) were used, respectively. Neither solution gave a precipitate after five days. Eventually, enough water evaporated from both solutions to give solid products.

COMPARATIVE EXAMPLE E

This example was run in the manner of Comparative Example B, except that purified [S,S]-EDDS acid was used. No precipitate formed over five days. After ten days enough water had evaporated to give a solid product.

COMPARATIVE EXAMPLE F

A 10-mL beaker was charged with [S,S]-EDDS acid (1.0 g, 3.4 mmoles); [R,R]-EDDS acid (1.0 g, 3.4 mmoles); and deionized water (5.0 g). The pH of the mixture was raised to 7.0 with 50 percent aqueous NaOH (1.15 g, 14.4 mmoles). Over several hours, a white precipitate formed. This was removed by filtration and dried to 0.85 g, amounting to 2.1 mmoles of rac-$Na_2EDDS\cdot4$ $H_2O$ (31% yield). Evaporation of the water resulted in the recovery of more product.

COMPARATIVE EXAMPLE G

A 100-mL beaker was charged with [S,S]-EDDS acid (10.6 g, 0.0363 mole); deionized water (12.8 g); and 50 percent aqueous NaOH (11.6 g, 0.145 mole). The mixture was stirred until all the acid had dissolved, and then concentrated $HNO_3$ was added to lower the pH to 7.0. No precipitate formed within 20 hours, even after the addition of (racemic/meso) $Na_2EDDS \cdot 4H_2O$.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A method for isolating a disodium salt of ethylenediamine-N,N'-disuccinic acid from an alkaline aqueous solution containing a mixture of racemic and meso isomers of sodium salts of ethylenediamine-N,N'-disuccinate comprising adjusting the pH of the alkaline solution to between about 5 to about 10 by the addition of an acid and recovery of the solid disodium salt.

2. The method of claim 1 wherein the racemic and meso isomers of ethylenediamine-N,N'-disuccinic acid are prepared by reacting sodium maleate with ethylenediamine in an aqueous solution.

3. The method of claim 1 wherein the acid is a strong mineral acid.

4. The method of claim 1 wherein the acid is hydrochloric, hydrobromic, sulfuric, nitric, phosphoric, perchloric, formic, acetic, chloroacetic, dichloroacetic, trichloroacetic, trifluoroacetic, propionic, butyric, methylsulfonic, trifluoromethylsulfonic, ethylsulfonic, methylphosphonic, and ethylphosphonic acids.

5. The method of claim 4 wherein the acid is sulfuric, nitric or hydrochloric.

6. The method of claim 5 wherein the pH is adjusted to between about 6 to about 8.

7. The method of claim 2 wherein the acid is a strong mineral acid.

8. The method of claim 2 wherein the acid is hydrochloric, hydrobromic, sulfuric, nitric, phosphoric, perchloric, formic, acetic, chloroacetic, dichloroacetic, trichloroacetic, trifluoroacetic, propionic, butyric, methylsulfonic, trifluoromethylsulfonic, ethylsulfonic, methylphosphonic, and ethylphosphonic acids.

9. The method of claim 8 wherein the acid is sulfuric, nitric or hydrochloric.

10. The method of claim 9 wherein the pH is adjusted to between about 6 to about 8.

11. The method of claim 1 wherein the disodium salt is the tetrahydrate.

12. The method of claim 2 wherein the ethylenediamine-N,N'-disuccinic acid formed is the tetrasodium salt.

13. The method of claim 1 wherein the disodium salt is a mixture of racemic and meso isomers.

14. The method of claim 2 wherein the ethylenediamine-N,N'-disuccinic acid formed is a mixture of racemic and meso isomers.

* * * * *